(12) United States Patent
Karp et al.

(10) Patent No.: US 8,596,135 B2
(45) Date of Patent: Dec. 3, 2013

(54) SYSTEM AND METHOD FOR MONITORING HEALTH OF STRUCTURAL JOINTS

(75) Inventors: Baruch Karp, Beer Sheva (IL); Daniel Rittel, Haifa (IL); David Durban, Haifa (IL)

(73) Assignee: Technion Research and Dvelopment Foundation Ltd., Haifa (IL)

( * ) Notice: Subject to any disclaimer, the term of this patent is extended or adjusted under 35 U.S.C. 154(b) by 596 days.

(21) Appl. No.: 12/519,243

(22) PCT Filed: Jun. 12, 2007

(86) PCT No.: PCT/IL2007/001508
§ 371 (c)(1),
(2), (4) Date: Mar. 16, 2010

(87) PCT Pub. No.: WO2008/068761
PCT Pub. Date: Jun. 12, 2008

(65) Prior Publication Data
US 2010/0162825 A1    Jul. 1, 2010

Related U.S. Application Data

(60) Provisional application No. 60/873,268, filed on Dec. 7, 2006.

(51) Int. Cl.
*G01L 1/00* (2006.01)
*G01L 1/16* (2006.01)

(52) U.S. Cl.
USPC ............... 73/781; 73/760; 73/788; 73/789; 702/34; 702/35; 702/42

(58) Field of Classification Search
USPC ............... 73/781, 786, 788, 789; 702/34, 42
See application file for complete search history.

(56) References Cited

U.S. PATENT DOCUMENTS 5,065,630 A * 11/1991 Hadcock et al. ............... 73/802
5,816,530 A * 10/1998 Grube .......................... 244/1 R
5,841,034 A * 11/1998 Ball ............................... 73/800

(Continued)

OTHER PUBLICATIONS

Giurgiutiu, Victor, Reynolds, Anthony, and Rogers, Craig. "Experimental Investigation of E/M Impedence Health Monitoring for Spot-Welded Structural Joints", Journal of Intelligent Materials Systems and Structures, v.10, pges 802-812 (1999).*

(Continued)

*Primary Examiner* — Leonard Chang
*Assistant Examiner* — Natalie Huls
(74) *Attorney, Agent, or Firm* — William H. Dippert; Eckert Seamans Cherin & Mellott, LLC

(57) ABSTRACT

The present invention provides a system and a method monitoring the health of structural joints by monitoring the strain developed near the joint due to perturbation applied away from that joint and comparing the monitored ratio between near field and far field strain to strain ratio which develops in a healthy joint due to comparable perturbation. The system for monitoring joints comprises: at least one near field strain measuring device installed near a monitored joint for monitoring the induced strain; at least one far field strain measuring device installed away from monitored joint indicating, measuring or producing the perturbation; and a data processor connected to said near field strain measuring device and to said near field strain measuring device for analyzing the response of the structure to the perturbation and determining the integrity of said joint.

25 Claims, 14 Drawing Sheets

(56) References Cited

U.S. PATENT DOCUMENTS

| | | | |
|---|---|---|---|
| 5,922,967 A * | 7/1999 | Motoyama | 73/794 |
| 6,006,163 A * | 12/1999 | Lichtenwalner et al. | 702/36 |
| 6,399,939 B1 * | 6/2002 | Sundaresan et al. | 250/231.1 |
| 6,996,480 B2 * | 2/2006 | Giurgiutiu et al. | 702/35 |
| 7,024,315 B2 * | 4/2006 | Giurgiutiu | 702/33 |
| 7,075,424 B1 * | 7/2006 | Sundaresan et al. | 340/500 |
| 7,089,124 B2 * | 8/2006 | Dong et al. | 702/42 |
| 7,263,446 B2 * | 8/2007 | Morin et al. | 702/34 |
| 7,276,703 B2 * | 10/2007 | Berkcan et al. | 250/358.1 |
| 7,343,265 B2 * | 3/2008 | Andarawis et al. | 702/188 |
| 7,458,266 B2 * | 12/2008 | Beard et al. | 73/579 |
| 7,558,701 B2 * | 7/2009 | Andarawis et al. | 702/183 |
| 7,571,058 B2 * | 8/2009 | Sealing et al. | 702/34 |
| 7,596,470 B2 * | 9/2009 | Kim | 702/183 |
| 7,660,496 B2 * | 2/2010 | Roberts | 385/13 |
| 2003/0009300 A1 * | 1/2003 | Giurgiutiu | 702/35 |
| 2006/0179949 A1 * | 8/2006 | Kim | 73/588 |
| 2006/0219026 A1 * | 10/2006 | Dong et al. | 73/808 |
| 2008/0061959 A1 * | 3/2008 | Breed | 340/539.1 |
| 2010/0063751 A1 * | 3/2010 | Korolev | 702/41 |
| 2010/0089161 A1 * | 4/2010 | Taheri | 73/588 |
| 2010/0238027 A1 * | 9/2010 | Bastianini | 340/540 |
| 2010/0262390 A1 * | 10/2010 | Caicedo et al. | 702/56 |
| 2011/0138918 A1 * | 6/2011 | Zagrai et al. | 73/588 |
| 2011/0202289 A1 * | 8/2011 | Kalantari Khandani | 702/42 |
| 2012/0203474 A1 * | 8/2012 | Kawiecki et al. | 702/39 |
| 2012/0271566 A1 * | 10/2012 | Deshmukh et al. | 702/42 |

OTHER PUBLICATIONS

Giurgiutiu, Reynolds, and Rogers, "Experimental Investigation of E/M Impedence Health Monitoring for Spot-Welded Structural Joints", 1999, Journal of Intelligent Materials Systems and Structures, v. 10, pp. 802-812.*

* cited by examiner

SYSTEM AND METHOD FOR MONITORING HEALTH OF STRUCTURAL JOINTS

CROSS-REFERENCE TO RELATED APPLICATIONS

This is a U.S. National Phase filing of co-pending PCT Patent Application No. PCT/IL2002/001508, filed Jun. 12, 2007, which is based on and claims the priority of U.S. Provisional Patent Application Ser. No. 60/873,268, filed Dec. 7, 2006.

FIELD OF THE INVENTION

The present invention relates to a system and method for non-destructively monitoring the integrity of structural joints and early detection of crack initiation and edge delaminations using at least one strain gauge.

BACKGROUND OF THE INVENTION

Many industrial structures include joints joining beams or plates. Often, these joints are load carrying and their integrity is critical to the strength of the entire structure.

While visible inspection is sometimes easy when the beam or plate is exposed, it is often hard or impossible to view the entire joint structure. For example, screws binding a beam may become partially loose or develop cracks, compromising the joint structural integrity without having any visible signs.

Often, the catastrophic breakdown of a structure starts with a failure of a weak or damaged joint. Often, integrity of a joint deteriorates due to fatigue, corrosion or mishandling such as incorrect assembly after maintenance action.

Methods for monitoring structural integrity have been developed, however there is a need for system and method for monitoring strength and integrity of a joint without the need to disassemble said joint.

Condition-based maintenance of structural components assisted by a real-time monitoring is a relatively new arena enabling cost effective maintenance and improved functional reliability of the structure. Emergence of this field has been enabled by intensive developments of Structural Health Monitoring (SHM) systems during the last few decades.

Several recent reviews discuss methods employed in detection, allocation, and evaluation of various types of structural damage [1-6]. Basically, SHM systems consist of a physical device for data collection and a signal-processing computer along, with an appropriate algorithm. Efficient identification of the onset of damage, or deterioration, at the earliest possible stage; centers on the sensitivity of a selected diagnostic parameter of structural response to the type of damage to be detected. That sensitivity is reflected in the design of the monitoring device and in the selected signal-processing algorithm.

Currently, SHM systems rely mainly on three diagnostic parameters considered as structural markers: modal properties of vibrating structures, propagation of Lamb waves, and impedance of the structure as sensed by attached PZT wafers.

Recently, Pandurangan and Buckner [7] suggested the use of modal damping ratios as another marker for monitoring single-lap adhesive joints. Their experiments reveal that the sensitivity of this method is favorable in comparison with frequency-based methods.

It should be noted that sometimes a small defect which causes a minor effect on the total strength of a joint, for example, a small crack at the joint, may develop rapidly under deteriorating conditions, causing catastrophic failure of the joint. Thus, it is important to detect, identify and correct a defect be tore its rapid progression.

REFERENCES

[1] O. S. Salawu, Detection of structural damage through changes in frequency: a review, Engineering-Structures 19 (1997) 718-723.
[2] E. P. Carden, P. Fanning, Vibration based condition monitoring: a review, Structural Health Monitoring 3 (2004) 3557-377.
[3] S. W. Doebling, Farrar, M. B. Prime, W. Daniel Shevitz, Damage identification and health monitoring of structural and mechanical systems from changes in their vibration characteristics: a literature review. LANL Report LA-13070-MS, 1996.
[4] C. R. Farrar, S. W. Doebling, D. A. Nix, Vibration-based structural damage identification, Philosophical Transactions of the Royal Society of London, Series A: Mathematical, Physical and Engineering Sciences 359 (2001) 131-149.
[5] H. Sohn, C. R. Farrar, F. M. Hemez, D. D. Shunk, D. W. Stinernates, B. R. Nadler, A review of structural health monitoring literature. 1996-2001, LANL Report LA-13976-MS, 2003.
[6] Z. Su, L. Ye, Y. Lu, Guided Lamb waves for identification of damage in composite structures a review, Journal of Sound and Vibration 295 (2006) 753-780.
[7] P. Pandurangan, G. D. Buckner, Vibration analysis for damage detection in metal-to-metal adhesive joints, Experimental Mechanics 46 (2006) 601-607.
[8] B. Karp, D. Durban, Evanescent and propagating waves in prestretched hyperelastic plates, International Journal of Solids and Structures 42 (2005) 1613-1647.
[9] B Karp, Dynamic version of Saint-Venat's principle-historical account and recent results, Nonlinear Analysis 65 (2005) e931-e942
[10] R. D. Gregory, F. Y. M. Wan, Decaying states of plane strain in a semi-infinite strip and boundary conditions for plate theory, Journal of Elasticity 14 (1984) 27-64.
[11] P. J. Torvik, The elastic strip with prescribed end displacement, Journal of Applied Mechanics, Transactions of ASME 38 (1971) 929-936.
[12] M. E. Ducan Fama, Radial eigenfunctions for the elastic circular cylinder, Quarterly Journal for Mechanics and Applied Mathematics 25 (1972) 479-495.
[13] C.-H. Wu, R. Plunkett, On the solutions of plates, strips, rods, and cylinders subjected to arbitrary dynamic edge load, SIAM Journal of Applied Mathematics 15 (1967) 107-119.
[14] W. M. Karunasena, A. H. Shah, S. K. Datta, Reflection of plane strain waves at the free edge of a laminated composite plate, International Journal of Solids and Structure 27 (1991) 949-964.
[15] R. D. Gregory, The general form of the three-dimensional elastic field inside an isotropic plate with free faces, Journal of Elasticity 28 (1992) 1-28.
[16] A. E. Vovk, V. V. Gudkov, T. V. Levchenkova, V. V. Tyutekin, Normal modes of a solid rectangular waveguide, Soviet Physics Acoustics 26 (1980) 194-198.
[17] M. M. Frocht Photoelasticity, Vol. II, Wiley, New York, 1948.
[18] E. R. Generazio, Overview of the National Aeronautics and Space Administration's Nondestructive Evaluation (NDE) Program, 38 Quality Assurance and Reliability, NASA, June 1999.

SUMMARY OF THE INVENTION

The present invention provide a System and a method for monitoring the health of structural joints by monitoring the strain developed near; the joint induced by perturbation applied away from that joint and comparing the monitored strain to strain which develops in a healthy joint due to comparable perturbation. The said method can also facilitate early detection of minor cracks developed at locations known in advance, edge delaminations of composites and conditions of over-stress exceeding yield; stress of the material.

In what follows the term "joint" refers also to "crack" and "edge of laminates". Near field refers also to the area close to crack and edge.

In one aspect of the invention, a system for monitoring joints is provided comprising: at least one near field strain measuring device installed, near a monitored joint, monitoring the induced strain; at least one far field strain indicating device installed away from monitored joint indicating, measuring or, producing the perturbation; and a data, processor connected to said near field strain measuring device and to said near field strain measuring device, analyzing the response of the structure to the perturbation.

In some exemplary embodiments, the near field strain measuring device is a strain gage.

In some exemplary embodiments, the near field strain measuring device is a non-contact device.

In some exemplary embodiments, the far field strain indicating device is a strain gage.

In some exemplary embodiments, the far field strain indicating device is a position sensor.

In some exemplary embodiments, the far, field strain indicating device is an accelerometer.

In some exemplary embodiments, the far field strain indicating device is an actuator.

In some exemplary embodiments, the far field strain indicating device is a static load.

In some exemplary embodiments, the strain in the structure induced by a static load.

In some exemplary embodiments, the strain in the structure induced by a dynamic load.

In some exemplary embodiments, the actuator generating dynamic load is a PZT actuator.

In some exemplary embodiments of the invention, evanescent waves are excited by strain generating device located in the far field and are monitored by the near field strain measuring device.

In some exemplary embodiments of the invention, evanescent waves are monitored by both far field strain indicating device and near field strain measuring device.

In other exemplary embodiments, the system further comprises a second near field strain measuring device.

In some exemplary embodiments, the second near, field strain device is installed near the same monitored joint.

In some exemplary embodiments, the second near field strain device is installed near a second monitored joint.

In some exemplary embodiments, monitoring joints comprises comparing readings of near field strain measuring device and far field strain indicating device to readings from a joint similar to the monitored joint.

In some exemplary embodiments; the monitoring joints comprises comparing readings of near field strain measuring device and far field strain indicating device to stored readings from said monitored joint.

Another aspect of the invention is to provide a method for monitoring joints comprising the steps of applying known stress at location far from the monitored joint; measuring strain caused by said applied stress at location close, to said monitored joint.

In some exemplary embodiments, the applied stress excites evanescent waves in the joined member.

In some embodiments the evanescent waves are time dependent.

In some embodiments the "evanescent waves" are time independent.

In some exemplary embodiments, the applied stress is static.

In some exemplary embodiments, the applied stress is dynamic.

In some exemplary embodiments, the applied stress is repetitive.

In some exemplary embodiments, the applied stress is induced by the vibration of the structure.

In some exemplary embodiments, the applied stress isn't harmonic.

In some exemplary embodiments, applying known stress comprises computing said stress from reading of a sensor located far from the monitored joint.

In some exemplary embodiments, the applied stress is caused by routine operation of said joint.

Another aspect of the invention is to provide a method for identifying flaws in a joint comprising the steps of: providing signal signature of a healthy joint; providing plurality of signal signatures of flawed joints; acquiring signal from a suspected joint; and comparing said acquired signal from a suspected joint with said signal signature of a healthy joint and plurality of said signal signatures of flawed joint.

In some embodiments, providing plurality of signal signatures of flawed joints comprises manufacturing or identifying flawed joints and acquiring experimental data from said flawed joints.

Alternatively or additionally, providing plurality of signal signatures of flawed joints comprises calculating the signal signatures of flawed joints by modeling said joint. In some embodiments modeling the joint is done using finite element method. In some embodiments modeling the joint comprises calculation of evanescent waves in the joined member.

It should be noted that, in general, stresses and strains are tensors. In the system and method of the invention, generated stresses and measured strains need not be collinear. For example, a plurality of strain measuring devices may be aligned at angles not parallel, or even perpendicular to each other.

Similarly, stress indicator devices and strain measuring devices may be angulated with respect to each other.

In some embodiments, the system comprises of at least two near field strain measuring devices located near the monitored joint, but at different locations such that perturbation in the near field strain distribution due to joint weakness may be detected.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. The same reference numbers are used to designate the same or related features on different drawings. The drawings are generally not drawn to scale. For clarity, some optional features may be drawn in dashed lines In the drawings.

DESCRIPTION OF THE PREFERRED EMBODIMENTS

Figure 1:
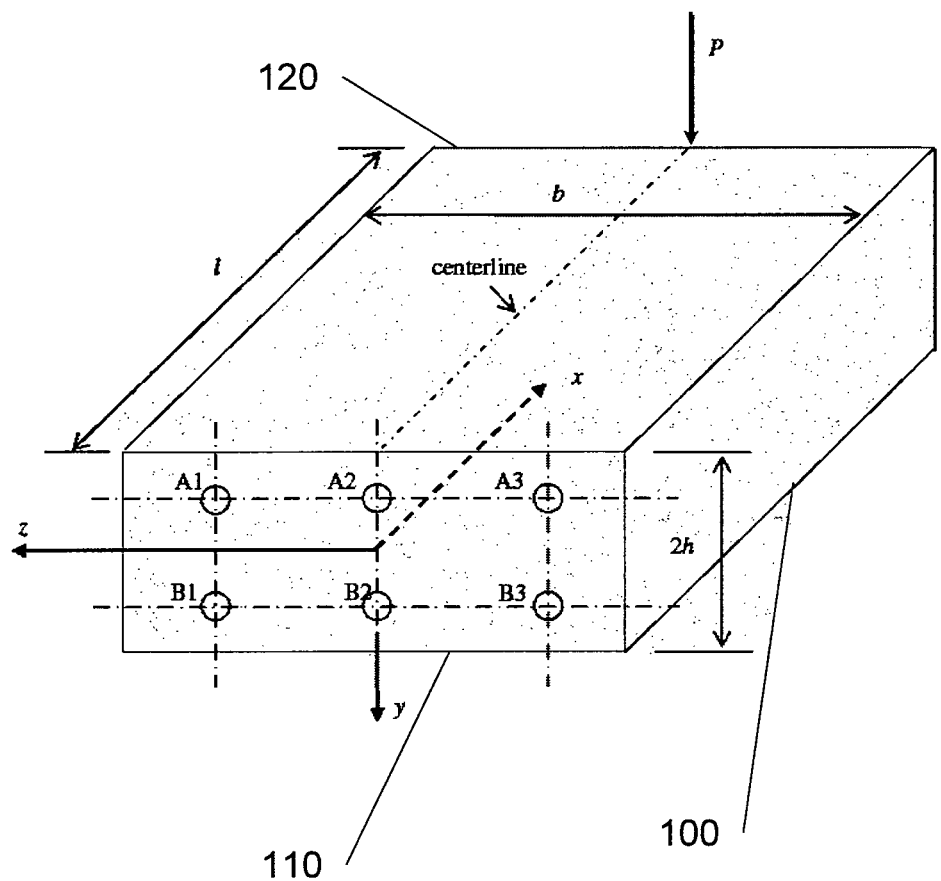
FIG. 1. depicts a schematic view of the elastic beam and the clamped end showing the coordinate system FIG. 2. schematically depicts experimental results of strain history at five stations for a sequence of removal and retightening of screws with an end load of 110 N.

The present invention relates to a system and method for nondestructively monitoring the integrity of structural joints by measuring the strain induced near the monitored joint. It also can be used to detect initiation of a cracking process (if the location of crack initiation is estimated in advance) and to detect edge delamination in composite beam-like and plate-like members.

Before explaining at least one embodiment of the invention in detail, it is to be understood that the invention is not limited in its application to, the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The drawings are generally not to scale. For clarity, non-essential elements were omitted from some of the drawings.

As used herein, an element or step recited in the singular and proceeded with the word "a" or "an" should be understood as not excluding plural elements or steps, unless such exclusion is explicitly recited.

Theory and Experimental Verification

In this section, the theory and feasibility study for employing end effects as novel diagnostic parameter (structural marker) for health monitoring of structural joints is presented. In a sense, these end effects can be considered as a special case of Lamb waves spectra. In contrast to the embodiments of the current invention, propagating waves are dominant in the design and analysis of existing SHM methods (e.g., Ref. [6]) whereas the emphasis here is on end, effects associated with evanescent Waves (e.g., Ref. [8]). These evanescent waves are generated at discontinuities, making the method of wide generality and applicability to several flaw types in a structure.

The proposed methodology is based on the known observation of high sensitivity of the near field to details of end data. Evanescent waves are generated at the ends of waveguides due to spatial incompatibility between the end data and the propagating modes. In statics this pattern falls under the study of Saint-Venant's Principe. In dynamics, although no agreed upon analogy to the static Saint-Venant principle has yet been found [9], the sensitivity as been observed in problems related to waveguides as, for example, in the split Hopkinson bar instrumentation. Traditionally, both in statics and in dynamics of structures, reliance on the response of the structure within the near field has not been of practical interest. Here, it is indeed this sensitivity to end data that is taken advantage of End effects are regarded as the joint signature and contain key data pertaining to the integrity of edge fixation.

1. Experimental Setup.

To investigate in laboratory tests the effect of damaged end conditions on near field effects, a cantilever beam with controlled damage of the clamping conditions was chosen.

FIG. 1. shows a schematic view of the elastic beam 100 and the clamped end 110 used for experimental verification, showing the coordinate system, the numbering of the six screws A1, A2, A3, B1, B2 and B3 at the clamped end 110, the load location at the free end 120, and centerline along which strain gauges were aligned.

At the free end x=1 either a quasi-static or dynamic bending load P is applied. In the experiments a beam with dimensions of l=655 mm, 2 h=25.4 mm, b=60 mm was used.

The dynamic response of a cantilever beam has been experimentally examined to demonstrate near field sensitivity to details of the end conditions (FIG. 1). "End conditions" are perceived here as a manifestation of the details of the joint, with possible deviations from the designed original configuration. In view of the analytical similarity between static and dynamic end effects (exponential decay in the axial direction), both static and dynamic experiments were performed. In the static experiments a weight was attached to the free end of the beam. In the dynamic experiments a short rod was dropped to hit the same free end of the beam.

Strains along the centerline of the beam were measured for repeated identical excitations with (controlled) different clamping conditions of, the built-in end. Five strain gauges were attached to the upper surface of the beam, three located within the immediate vicinity of the clamped end (near field) and two at a distance from it (far field).

Clamping of the beam is achieved by six screws, shown in FIG. 1. Various combinations of tightness of the screws were considered as simulating different conditions. It is noted here that "clamping" is a term used in practice with no definite meaning within the theory of elasticity. For the purpose of the present document the phrase "clamping condition" will be used to discriminate between various ways in which end fixation realized, all of which could be considered as "clamping" for practical engineering purposes. Various levels of tightness of the screws can be regarded as different end conditions and as artificially induced damage to the joint, simulating events such as loosening of bolts, debonding, cracking, or loss of rivets.

Recalling the axial decay of eigenfunctions in static fields, and the existence of evanescent waves in the dynamic response, it is expected that at least part of the strain history readings will reflect the controlled changes in clamping conditions.

The main result emerging from this verification study is that simple experimental techniques, along with monitoring of surface strains in the near field, enable the identification of even minor changes in the joint condition. In the static experiments the condition of completely and partially loose screws was identified. In the dynamic experiments completely loose screws were identified clearly with less conclusive results for partially loose screws. These observations agree well with the analysis of end, effects given in the theoretical section herein.

In both the static and dynamic experiments; the far-field measured data of strains was found to be insensitive to fine details in the clamping condition. Far-field response is influenced only when more than one screw is missing. This condition departs considerably from what would be considered as clamping from the engineering practice point of view.

2. Analytical Construction of End Effects

End effect is a common synonym to Saint-Venant's principle (SVP), according to which the strains and the stresses at points located far from the loaded end are determined uniquely by statical equivalents of the applied edge load and are not affected by the spatial distribution of the load. End effects can be viewed as the near edge strain perturbations, induced by small changes in end data, and decaying in the axial direction. Here, the formal representation of these end effects is summarized briefly, both for static and dynamic loadings.

2.1. Static End Effects

The solution of plate problems is common partitioned into two parts e.g., Ref. [10]) the inner solution and the outer solution. The simplest inner solutions of plane problems are given analytically by polynomial solutions of the bi-harmonic equation. The axial strain for an elastic, isotropic cantilever plate subjected to bending by a dead load P applied at its free end, under plane strain conditions, is given by $$\varepsilon_x(x, y) = \frac{(1-v^2)(l-x)P}{EI} y,$$

where E is Young's modulus, v is Poisson's ratio, and l and 1 are the inertia and length of the beam, respectively. Here x, y denote the axial and transverse coordinates with the origin at the center of the built-in end (see FIG. 1).

Expression (1) is exact everywhere within the plate as long as the boundary conditions comply with this solution-linearly distributed-axial stress and parabolic distribution of shear stress at the clamped end, and zero axial stress with a parabolic distribution of the shear stress at the loaded end.

If clamping is realized in a way that the distribution of the boundary stresses across the thickness deviates from the inner, solution, end effects will be generated and expression (1) will no longer be accurate close to the vicinity of the edge. The actual stress at the end can be viewed as a superposition of two stress distributions: one complying with the inner solution with static equivalents identical to those of the original stress distribution, while the other distribution has zero resultant force and moment. That second, self-equilibrated, load will induce end effects regarded as the outer solution for a given load. The displacement field describing these end effects for a semi-infinite plate is given by $$u(x, y) = \text{Re}\left\{\sum_n A_u U_n(y) e^{i\xi_n x}\right\}, \quad (2)$$

where $\xi_n$ are the (complex) eigenvalues of the Fadle-Papkovich equation, $U_n(y)$ and $A_n$ are the eigenfunctions and their amplitudes, respectively. Here $U_n(y)$ stands for a vector consisting of the x and y components of the displacement vector u. Complex eigenvalues $\xi_n$ make the solution (2) to decay in the axial direction x. The eigenvalue with the smallest imaginary part ($\xi_1$) dictates the extent of the outer solution—the largest distance from the end at which these decaying eigenfunction might have a non-negligible effect. Assuming the extent of the outer solution to be significantly smaller than the plate's length l, the complete expression for the axial strain in the vicinity of the clamped end can be written as $$\varepsilon_x(x, y) = \frac{(1-v^2)(l-x)P}{EI} y + \text{Re}\left\{\sum_n A_n i\xi_n U_n^x(y) e^{i\xi_n x}\right\}, \quad (3)$$

where $U_x^n$ is the axial component of eigenfunction. It is understood of course that, in general, end effects will be induced at the loaded end x ¼ l as well. However for future reference these end effects are omitted from Eq. (3) as they are not expected to practically influence the field in the vicinity of x=0.

Several methods are available for calculating the amplitudes $A_n$ in a semi-infinite plate (e.g., Refs. [11,12]). In these methods the resulting amplitudes should be such as to describe the detailed transversal distribution of the load (or displacement) at the edge x=0. It is clear therefore that any alteration of load distribution over the width 2 h will result in a change of the amplitudes. The eigenvalue with the smallest imaginary part dictates the upper bound on the smallest decay rate and has a value of 2.106/h for an elastic isotropic material. It follows that the eigenfunctions induce only insignificant contribution to the strain field beyond 1-2 beam widths. Any change in amplitudes $A_n$ will be significant only within that small range—the outer solution.

Therefore, measurable changes of strains in the near field which are not accompanied by (practical) change of strains in the far field can be attributed to modification of end data leaving the static equivalents unaltered.

2.2. Dynamic End Effects

Dynamic steady-state (harmonic) displacementfields in a semi-infinite plate are commonly expressed by separation of variables $$u(x, y, t) = \text{Re}\left\{\sum_n A_n U_n(y) e^{i(\xi_n x - \omega t)}\right\}, \quad (4)$$

Where $\xi_n$ are the wavenumbers that solve the Rayleigh-Lamb frequency equation for any given frequency $\omega$, $U_n(y)$ and $A_n$, are the wave mode vector and its amplitude, respectively, The spectral decomposition (4) can be considered as a dynamic generalization of the static solution (2). We use here the same notation $\xi_n$ for wavenumbers as for eigenvalues in Eq. (2) as they bear the same meaning and coincide numerically upon reducing the Rayleigh-Lamb equation to the static, case by taking frequency $\omega$ to zero. Methods for evaluating the amplitudes of the modes are similar to those used in the static case (e.g.; Refs. [1314]), thus connecting the spatial distribution of the end data with the amplitudes of the evanescent waves. That connection facilitates the nature of end effects as a structural signature of end data.

Contrary to the static case, the full spectrum of wave numbers includes real valued roots ($\xi_n$) that correspond to propagating waves, which convey energy into the far field. The evanescent waves associated with complex and purely imaginary wave numbers generated the end effects. This distinction between the two types of waves enables us to rewrite the solution (4) in the form $$u(x, y, t) = \text{Re}\left\{\sum_{n=1}^{N} A_n U_n(y) e^{i\xi_n x} + \sum_{n=N+1}^{\infty} A_n U_n(y) e^{i\xi_n x}\right\} e^{i\omega t}, \quad (5)$$

where the first summation is over the N real valued wavenumbers available at a given frequency $\omega$, while the second summation is over an infinite number of complex and purely imaginary wavenumbers. The propagating modes exhibit of course no attenuation (elastic response is assumed) in the axial direction of the plate, and therefore determine far-field response. In a finite plate these modes develop eventually into vibration. The axial decay rate of the evanescent modes is highly sensitive to the excitation frequency, with very small values of imaginary parts of the wavenumbers at some frequencies. Thus, no general conclusion relating to their maximal penetration depth can be reached in analogy with the static case [8]. Nevertheless, because the smallest imaginary part of the wavenumbers is of the same order as in the static case, it can be expected that these attenuating waves will affect the strain field at least within the distance of 1-2 plate depths.

Solution (5) describes a steady-state response to harmonic excitation, with a given single frequency. Transient fields are taken as a superposition of these steady-state solutions according to the Fourier theorem. Therefore, the observation that any change in the details of the end condition will influence amplitudes of the evanescent modes should be valid also for transient fields. Thus, as for the static case, if such changes in amplitudes of strain components, in the near field, can be detected by some sensitive device with no practical changes in strain readings appearing in the far field, for the same dynamic excitation, changes in end data can be inferred.

It should be mentioned that expressions (1)-(5) are valid under the assumption of plane strain conditions. The experiments, on the other hand, were performed with a beam, of finite width, for which neither plane strain nor plane stress can be justified. Representation of end effects, equivalent to those given in Eqs. (2) and (5), for a three-dimensional beam (neither plane stress nor plane strain) is given by Gregory [15] for quasi-static loading and by Wu and Plunkett [13], or by Vovk et al. [16], for dynamic response. The main added feature in the three-dimensional analysis is that the eigenfunctions (or wave modes) U(y) become also dependent on the z-coordinate. That modification does not alter the fundamental property of end effects, discussed earlier, for plane problems as being structural markers reflecting details of end conditions.

3. Experiments 3.1. The Setup

In the design of the experiments the aim was to examine how different clamping conditions will influence the strain field within a plate subjected to transverse load. Particularly, we wished to, demonstrate the sensitivity of the surface strain in the vicinity of the clamped end of the beam to different ways in which clamping is realized. No attempts were made to make quantitative assessments or to develop predictive tools, as those are expected to be tailored for each specific application. The particular function required of the system is to record surface strain response in the near and far fields of a beam subjected to identical static loads and dynamic excitations for various clamping conditions.

A cantilever beam made of Aluminum alloy 6061-T3 (E=69.3 GPa, U=0.33), with, dimensions detailed in FIG. 1, is clamped with the aid of 6 screws, arranged in two rows, to another vertical beam. The reference state of all screws. "tight-in" is considered as a baseline clamping condition. Controlled variations of clamping conditions were achieved by unscrewing, either partially or completely, one or more screws.

Static and dynamic loads were applied at the free end of the beam. Five strain gauges with a gauge length of 2 mm were attached to the upper surface of the beam along its centerline at distances of 5.7, 12.5, 25.4, 100, 200 mm from the clamped end 110 (corresponding to non-dimensional distances x/2 h of 0.2244, 0.9, 1, 4, 7.9) and designated here as stations 1 to 5, respectively. The strain gauges were sampled at the rate of 100 kHz/16-bit with a gain of 200. For static loads the signal was averaged 1000 times to improve signal to noise ratio.

3.2. Quasi-Static Experiments

The static load was chosen to be a transverse dead load applied at the free end (x=l) to induce bending of the beam. An appropriate weight was hinged on a screw located at the centerline of the beam at the free end 120.

The experiments consisted of repeating the static loading for various (controlled) clamping conditions. To simulate practical situations of damage two cases of missing screw(s) were tested: releasing the screws prior to loading and changing their tightening while the beam is under constant load. The first set of experiments examined the on/off condition of the screws while in the second set the ability to identify different levels of tightness was addressed. For that purpose a torque-meter was, used tightening the screws. The strains expected to develop within the beam are as predicted by (3)

with some deviation attributed t6 the three-dimensional nature of the field within the beam.

It should be noted that the strains within the beam do not vanish ever) if no load is applied at its end at x=l (and with gravity being neglected). This is due to the self-equilibrated load applied at the built-in end by the screws, leaving (3) only with the second term of summation over the eigenfunctions. For that reason the reading of the gauges in the dynamic experiments had to be readjusted, to zero following any change in the clamping conditions.

3.3. Dynamic Experiments

As a simple way of providing dynamic excitation, an impact by an aluminum rod (length 158 mm and diameter 12.5 mm) at the free end 120 of the beam 100 was used. The impacting rod was, dropped from the height of 27575 mm above the beam generating a bending pulse with an approximate duration of 50 ms, Repeated impacts were avoided by catching the rod upon its bouncing off the beam. Since repeat ability of the excitation is critical in interpretation of the experiments, an attempt has been made to generate as identical an input as possible. Although a simple device for marking the drop position was used, this handy method of dynamic excitation was not expected to deliver a highly repeatable input, and probably inferior to the widely used pulse generators (i.e., PZT). Nevertheless, the simple procedure employed turned out to be satisfactory for the purposes of this research.

The beam with various clamping conditions was excited by dropping the aluminum rod, approximately from the same height, to hit the centerline of the free edge of the beam. Each drop was considered as a single experiment. This excitation generated bending waves, which propagated towards the clamped end and back, eventually inducing vibration of the beam. Due to the transient nature of the response, the signals recorded are the superposition of eigenfields expressed by the summation (5), for as many frequencies as contained in the excitation itself it should be noted that evanescent waves are expected to be induced also at the free end of the beam x=1. It is assumed however that these evanescent waves have no influence on all five strain gauge readings, which are located closer to the clamped end. It is worth noting that though the strain gauges in the near field were expected to record superposition of incoming and reflecting signals, it does not impair, the purpose of the research, as no interpretation of that superposition attempted here.

Strain gauges readings were zeroed prior to each experiment, to cancel out the shift of the output, induced by quasi-static Change of strains due to removal of screws. Repeatability of the system was Checked at various stages of the experiment and used for interpretation of the results.

4. Experimental Results 4.1. Static Loading

Figure 2:
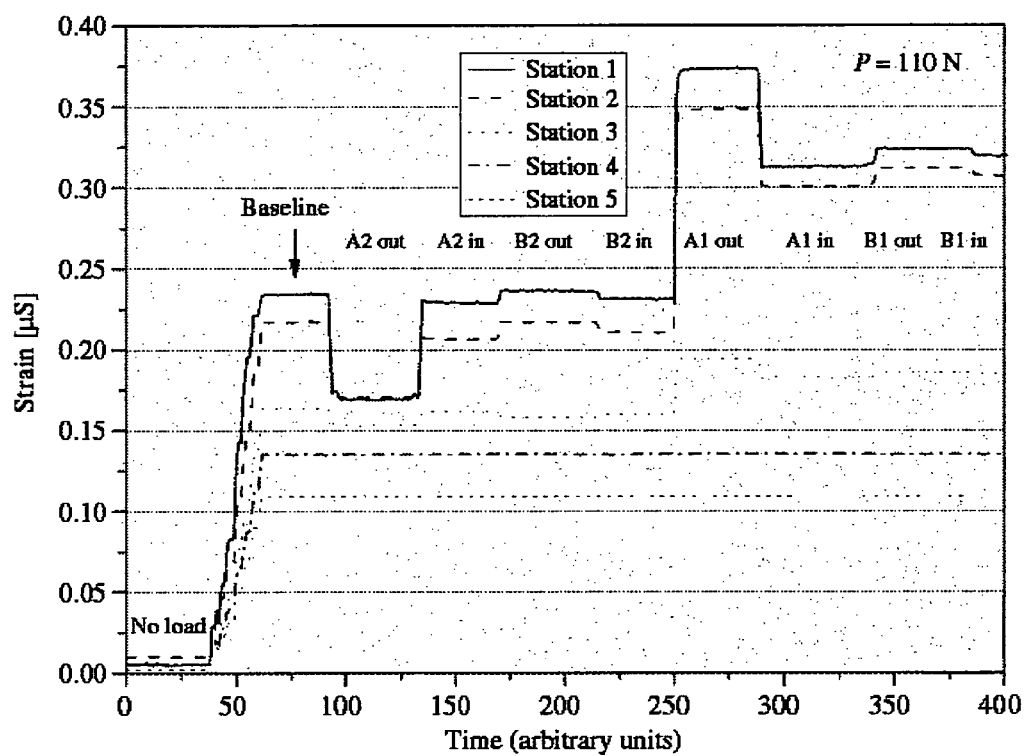

The beam was loaded statically by a dead load of 110N at its free end. Then, the screws were loosened and retightened back, one, at a time. The strain history of that sequence was traced in FIG. 2. The figure shows clearly that, as expected, the three strain gauges located within the near field (stations 1, 2, 3) responded significantly to the removal of each screw. Release of the screws in row B, located at larger distances from the strain gauges (screws B1 and B2), induced smaller effects than those closer to the strain gauges (screws A1 and A2). This difference is probably due to compression below the neutral plane, leaving screws in row B only with secondary function as compared to the function of the screws in row A. For future reference it is noted that the effect of missing screws B1 and B2 is practically identical. As expected, the two strain gauges at stations 4 and 5, located in the far field, did not record any change of strain due to, changes in the clamping condition. Some hysteresis upon retightening the screws can be observed, probably due to uncontrolled screwing moment at this stage of the experiments.

Figure 3:
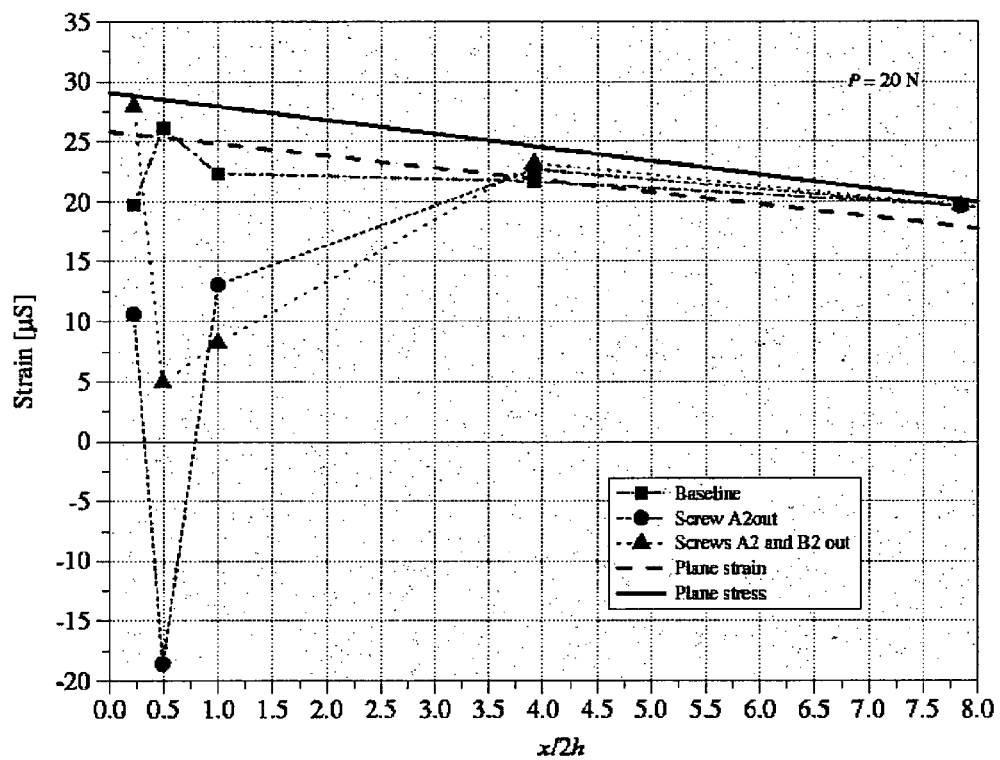
FIG. 3. schematically depicts experimental results of strain at five stations for three clamping conditions (baseline, missing screw A2, missing screws A2 and B2) with an end load of 110 N.
Figure 4:
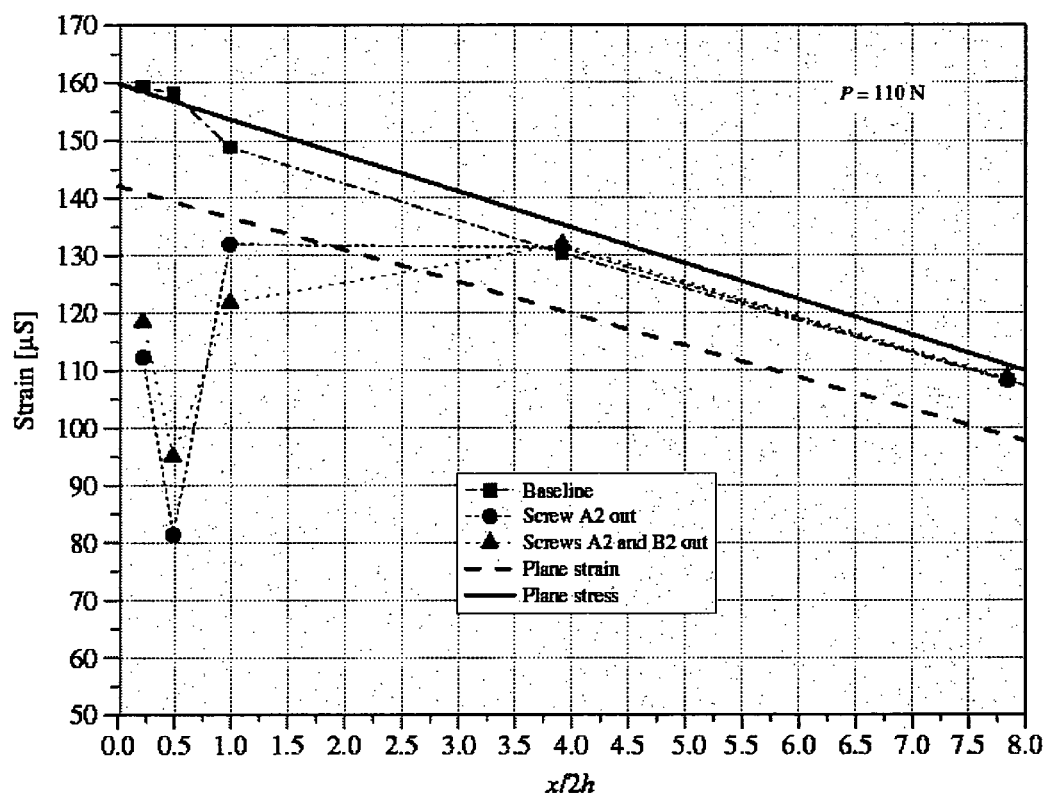
FIG. 4. schematically depicts experimental results of strain at five stations for three clamping conditions (baseline, missing screw A2, missing screws A2 and B2) with an end load of 110 N.

Strain recordings for the beam when loaded with 20 and 110N for three clamping conditions are shown in FIGS. 3 and 4, respectively. Theory of elasticity solutions, for the bending problem, in plane stress and plane Strain, are given by $$\varepsilon_x(x)|_{y=h} = \frac{(l-x)P}{EI} h \text{ plane stress,} \quad (6)$$

$$\varepsilon_x(x)|_{y=h} = (1-v^2)\frac{(l-x)P}{EI} h \text{ plane strain} \quad (7)$$

and displayed in FIGS. 3 and 4, the two loads. The connecting lines between the measurement points are for the sake of visualization. As expected, the recordings of strain gauges in the far field (stations 4 and within the limits of the prediction given by the theory of elasticity (6) and (7). Recordings of the gauges located in the near field (stations 1-3) deviate significantly from both these lines and from the straight line that could be extrapolated based on measurements at stations 4 and 5. That deviation indicates the dominance of the decaying modes, of the type given by Eq. (2), over the inner solutions (6) and (7), in the surface strain within the immediate vicinity to the joint. A discussion of FIGS. 3 and 4, in relation to Saint-Venant's principle, will be given later.

Figure 5:
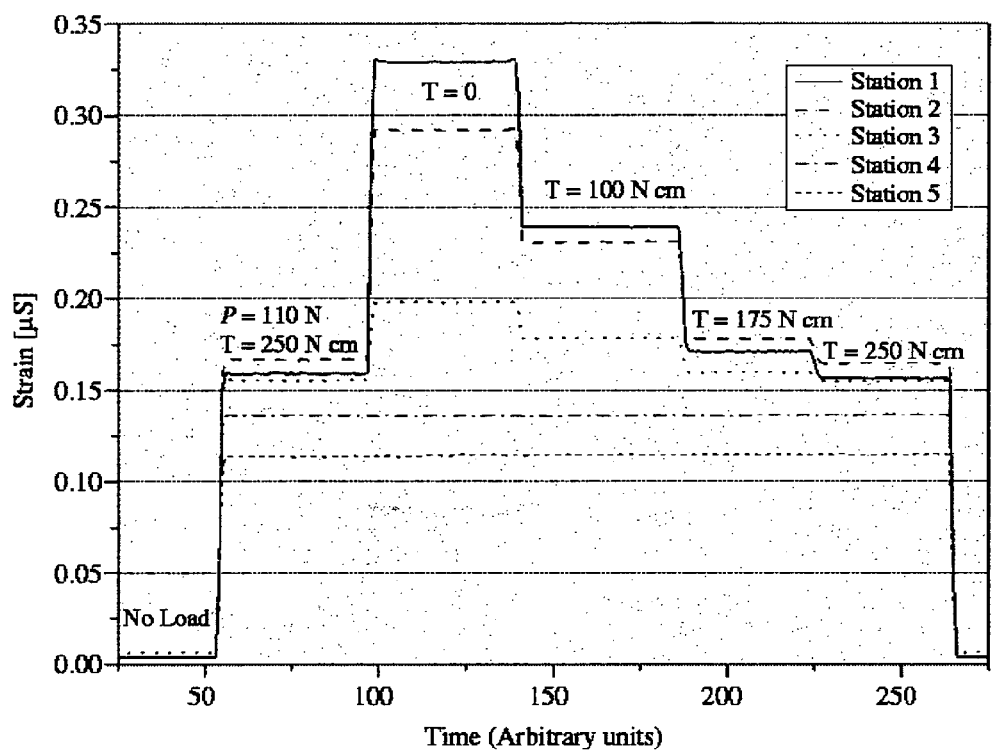
FIG. 5. schematically depicts experimental results of strain at all five stations for a sequence of torque levels T (N cm) of screw A3 wherein the beam is loaded by a dead load of 110 N.

FIG. 5 shows recordings of, all 5 stations for a sequence of different torque levels of screw A3 while the beam is loaded with 110 N. Prior to application of the load the screws were tightened with a torque of 250 Ncm and the strain gauge readings were zeroed. Then the beam was loaded, screw. A3 was removed completely followed by its retightening, with intermediate pauses at torque levels of 100, 175 and back to 250 Ncm.

It may be concluded from these results that it is possible to identify changes in the clamping details (joint condition). Such detection of even relatively small changes in the joints is based on the measurements of strain within the range of dominant end effects. Measurements taken from regions located far from the joint do not provide a similar indication.

4.2. Dynamic Loading

Figure 6:
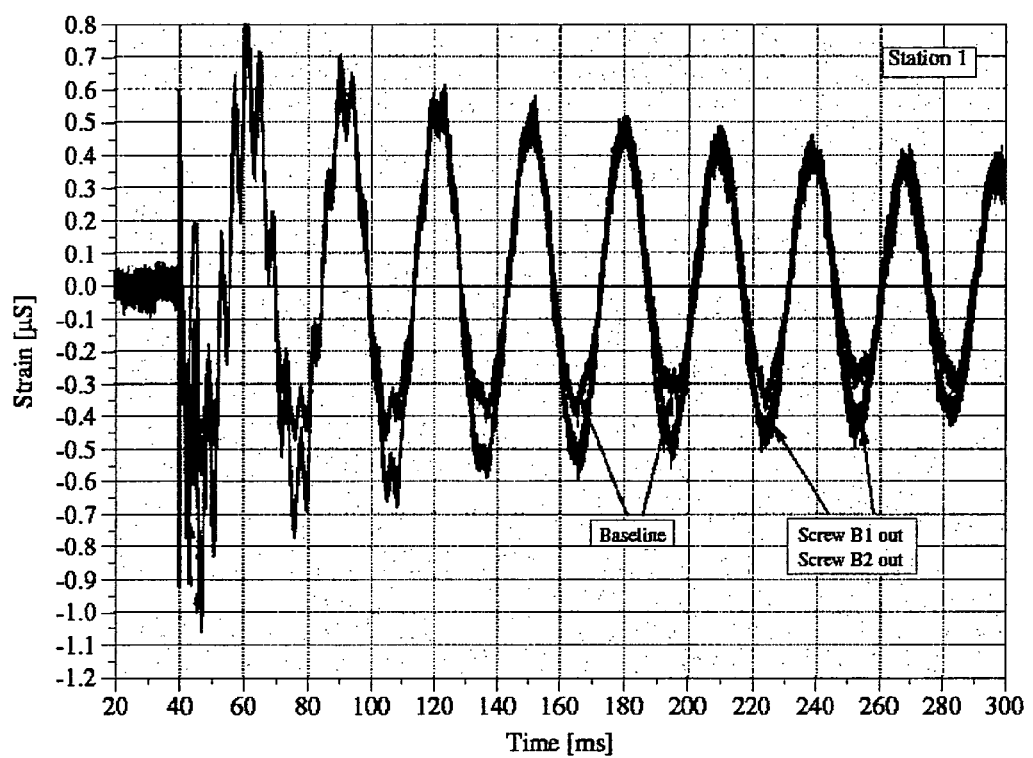
FIG. 6. schematically depicts experimental results of strain at station 1 for three identical experiments with different degrees of clamping showing that the recordings for screws B1 out, and B2 out, are almost identical.

A typical long-time strain history for the dynamic experiment is shown in FIG. 6 for three different clamping conditions. The first vibration mode is clearly visible with a natural frequency of 33 Hz—lower than the Calculated one (50 Hz) due to flexibility of the supporting beam. A pattern of almost pure vibration is. Observed after three time period (≈90 ms). It takes approximately 0.2 ms for a shear wave and 0.1 ms for longitudinal wave to travel across the length of the beam. Therefore, the recording at any station within the time interval of 30 ms is a superposition of several waves propagating in opposite directions, making a direct connection between the recordings and the displacement-field (5) impractical. Yet, some conclusions can be inferred since the amplitude of the recorded signal is a superposition of all available modes at all excited frequencies. This will be done by, focusing mainly on the amplitude of the response within the first 10-20 ms of the transient response.

Figure 7:
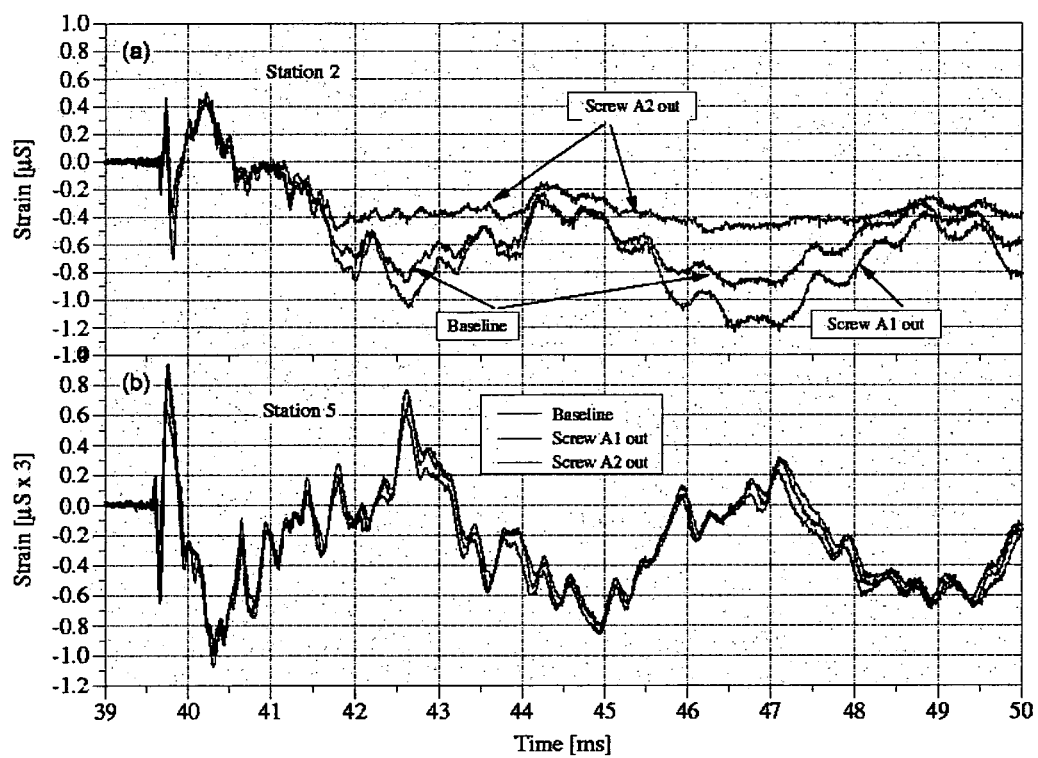
FIG. 7. schematically depicts experimental results of strain at stations 2 and 5 for baseline clamping and for clamping without screws A2 or A1: 7(a) station 2; and 7(b) station 5.

The dynamic response at stations 2 and 5 for baseline and clamping without screws A2 or A1 are shown in FIG. 7. At station 5 no difference in response for these three clamping conditions can be noticed, while at station 2 deviation from the baseline is significant, as can be judged from repeated experiments.

Repeatability of the recordings at station 2 for baseline (three identical experiments) and for missing screw A1 (two experiments) were performed. The results for different clamping conditions at station 5, as shown in FIG. 7*b*, fall within the scatter of experimental repeatability and therefore different clamping conditions cannot be inferred from measurements at station 5.

It is instructive to compare the recordings of FIG. 7*a* with those of FIG. 7*b* in view of the partition into two types of waves, as given by Eq. (5). Assuming that station 5 lies in the far field, it is not influenced by end effects and consists only of propagating waves contained in the first summation of Eq. (5). Previous results for static loading, as well as numerical values of complex wavenumbers [8](with the exception of small frequency range adjacent to cut-off frequencies) support this assumption. Thus, identical strain responses recorded at station 5 (FIG. 7*b*) for different clamping conditions can be attributed to generation of the same N propagating wave modes with identical amplitudes for all three different clamping conditions. It may be argued therefore that dynamic excitation applied at the end is practically identical for all experiments shown in FIG. 7

The recordings at station 2 (FIG. 7*a*) are a superposition of all available modes and frequencies. Here, unlike readings at station 5, the strain amplitude is a superposition of propagating and evanescent waves. Thus, the Partition of Eq (5), together with the conclusion that the excitation is practically identical (identical propagating waves), leads to conclusion that the different recordings at station 2 are due to different generation of evanescent waves. This as expected, makes the connection between the joint condition and the evanescent waves in analogy with the static experiments.

Recording for baseline clamping at station 2 was compared with the recordings for clamping when one of the lower screws (B1 or B2) is missing. Only minor changes in response due to the absence of screws B1 or B2 were noticeable in agreement with the static results shown in FIG. 2. Recording of these two cases for stations 1 and 3 are given in FIGS. 8 and 9, respectively. It can be observed that the strains at station 1 are sensitive enough to enable identification of missing screws B1 and B2, though recordings for the later two are indistinguishable. Similar effects induced by missing screws B1 and B2 could be expected from the static results in FIG. 2. Taking out screws B1 or B2 does not alter significantly enough the reading at station 3, neither in the static case (FIG. 2) nor in the dynamic case (FIG. 9) (though in the static case a small change is noticeable).

Figure 8:
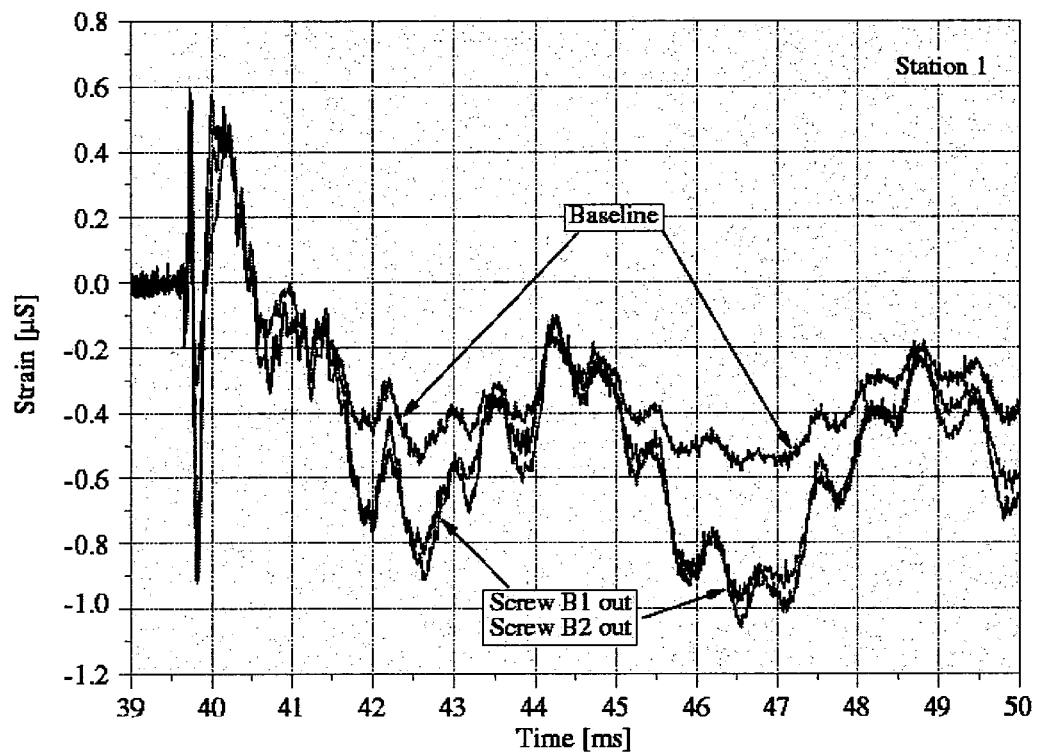
FIG. 8. schematically depicts experimental results of strain at station 1 for baseline clamping and for clamping without screws B1 or B2 showing that the recordings for screws B1 out, and B2 out, are almost identical.
Figure 9:
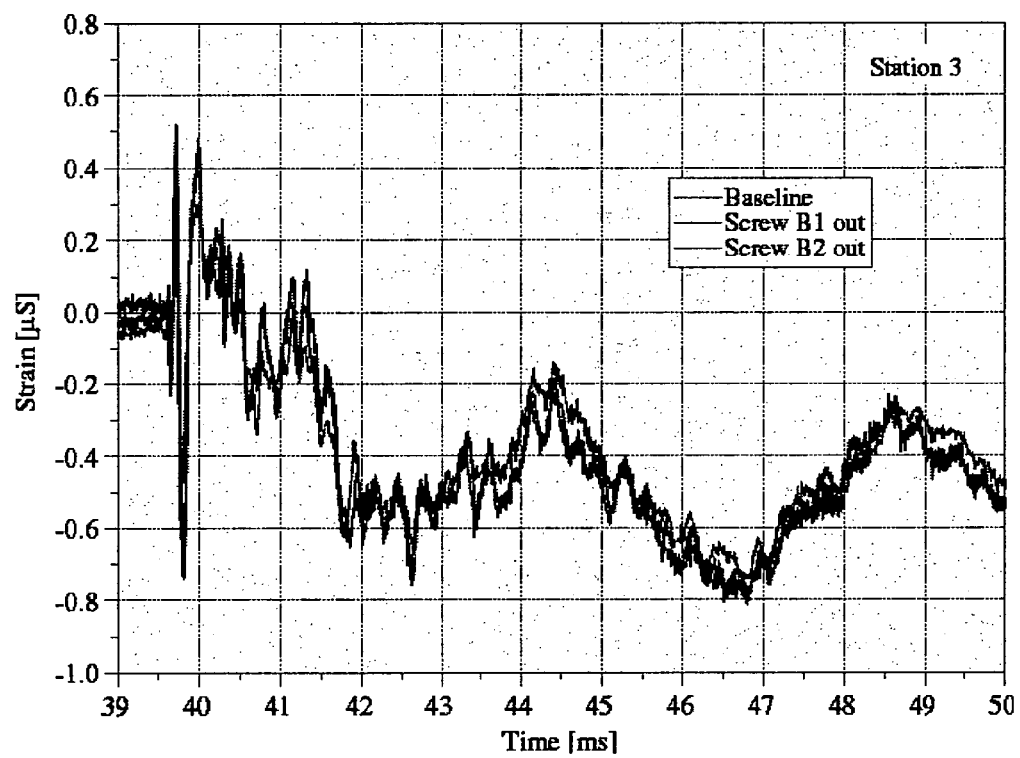
FIG. 9. schematically depicts experimental results of strain at station 3 for baseline clamping and for clamping without screws B1 or B2 showing that the three recordings are indistinguishable.

FIG. 8 displays the zoom-in of the first 10 ms of the response shown in FIG. 6. We find that for both short-time and long-time response, it is possible, to distinguish between the baseline condition and the state of Missing screws. It is apparent from FIG. 6 that the frequency of this vibration mode is not altered by removal of one screw from the lower row B. This suggests that the amplitude of the strain in the near field is more sensitive to small changes in the joint, as compared with the natural frequency. It appears that the amplitude of the strain in the near field is preferable to the natural frequency, as a marker for the joint condition. Moreover, either steady state or transient response of the beam can be used for health monitoring, if the diagnostic parameter is the near field amplitude.

Figure 10:
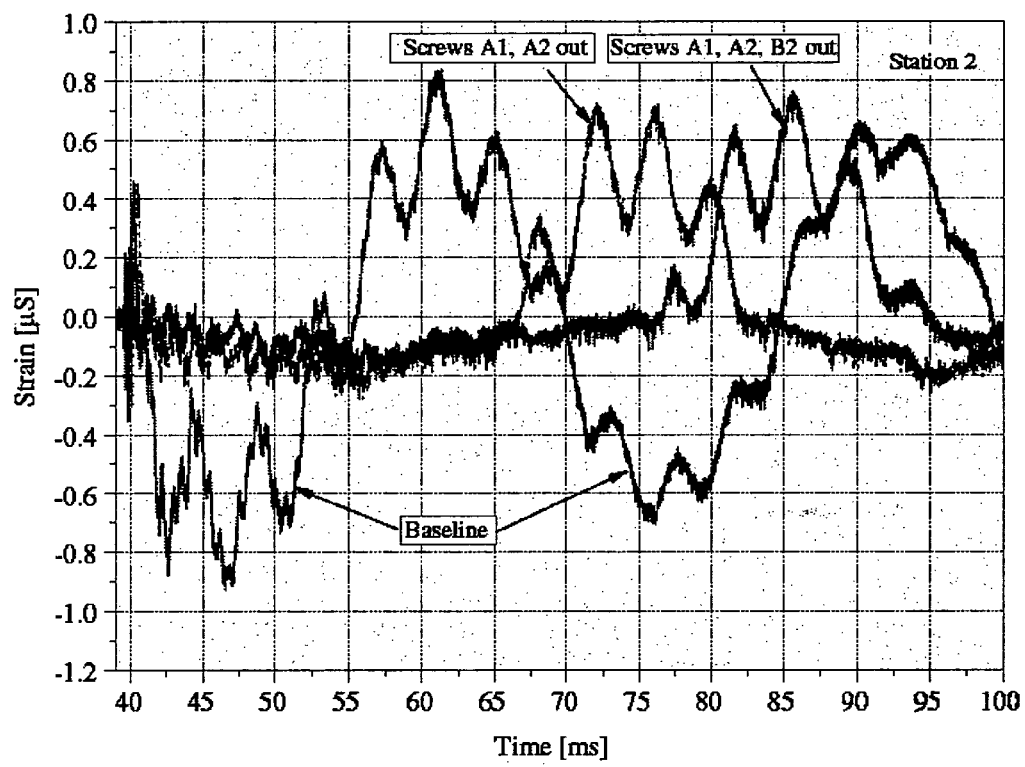
FIG. 10. schematically depicts experimental results of strain at station 2 for three clamping conditions with more than one screw missing.

Recordings at station 2 for two cases, when two, or three screws are Missing, are compared with the baseline state in FIG. 10 pattern is considerable, accompanied by profound change in the natural frequency of vibration: ensure repeatability, after the recordings of FIG. 8, all screws were put in place and the original signal was recovered. The shift in the natural frequency, induced by relatively large changes in joint condition, leads to vibration-based diagnostic methods, which is fully supported by this study. An equivalent reliance on natural frequency as a Marker for minor changes in joint conditions, as revealed in FIGS. 6-9, does not appear to be feasible. That observation will be supported by an FFT analysis in the next section.

5. Discussion

The static phase of the experiments was designed primarily in order to assess the sensitivity of the system subsequently employed in dynamic experiments. It was expected, from the similarity of Eqs. (3) and (5), that joint damage detectable by static experiments will be exposed with dynamic loading as well. The static measurements shown in FIGS. 2-5 display considerable sensitivity of the near field to complete absence of a single screw at various locations, and even to partially loosened screws. Moreover, loss of screws located in the compressive region (row B), where the screws have a smaller contribution to the joint's rigidity, is also detectable by measurement of surface strain in the near field.

Inter alia, FIGS. 3 and 4 provide an interesting demonstration of regions of validity of Saint-Venant's principle: Existing experimental demonstrations of the Saint-Venant region are based mainly on the photo-elastic method [17]. Deviations of measured surface strain from the linear predictions (6) and (7) illustrates the extent of the Saint-Venan't region which is definitely larger than one height of the beam (2 h).

Interpretation of the dynamic experiments relies here on both the pattern and amplitude of the signal, in time domain of near field strain. FIG. 10 shows an extreme response that occurs when the clamping condition is substantially altered. It can be easily detected by strain gauges located in the near field, when the structure is dynamically excited. However, such a large change in clamping condition is also recorded by the remote stations. Thus, there is no gain in locating strain, gauges in the near field when large changes in the joints' rigidity are to be monitored.

A more subtle result is sought when only small changes in joint strength take place, such as the loss of only one screw that might not be detectable by gauges located in the far field FIGS. 7*a* and 8 show that removal of a single screw, either in the tensile or in the compressive regions of the built-in edge, alter significantly the pattern of surface strain response in the near field but not in the far field. In the analogy with the static case, the dynamic near field differs from the far field by active decaying modes, which reflect details of the end data.

That connection between end conditions and evanescent waves justifies the use of end effects as a joint signature, which serves as a Marker for monitoring the joint condition.

In FIGS. 7-10 we have focused on transient response of the beam, which can be achieved in practice by a pulsating wave generator. Comparing-FIG. 6, which is typical to a vibrating structure, with FIG. 8 we find that screw removal can be detected either by inspection of the transient response or through the steady-state vibration. Hence, when the structure vibrates during its operation it should be possible to identify changes in joints condition without resort to auxiliary dynamic excitation. On the other hand, if the structure does not vibrate, as is often the case with space structures, small devices generating propagating Lamb waves directed toward the joint will serve the same diagnostic purpose. That, of course, is in cases when static measurements are not a feasible possibility.

An interesting difference between static and dynamic experiments is the higher sensitivity of static tests that enabled detection of low levels of tightness of screws. It is expected that with some minor improvements of the equipment (e.g. smaller strain gauges and more repeatable dynamic excitation) it will be possible to detect partially loose screws in dynamic tests as well.

It is of interest to compare the above analysis of near field response in the time domain with vibration-based measurements. To this end an FFT analysis was performed on the data of the experiments shown in FIG. 7.

Figure 11:
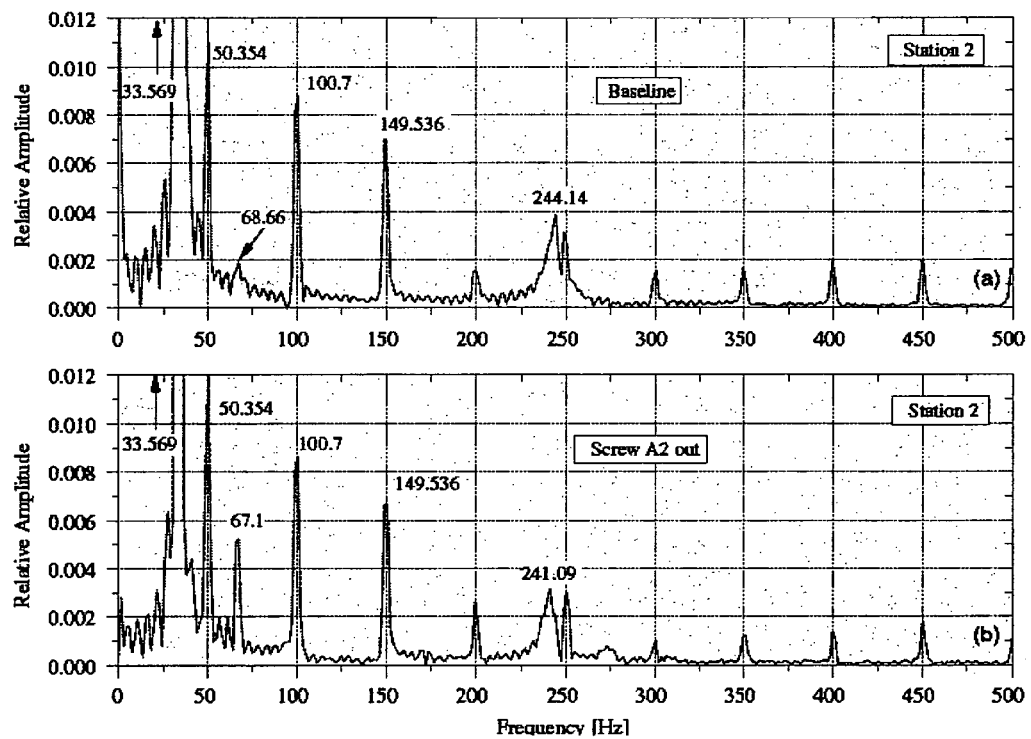
FIG. 11. schematically depicts FFT of experimental results of the recording at station 2: 11(a) for baseline clamping; and 11(b) for clamping with missing A2 screw.

The corresponding FFT plot of the recording at station 2, the time domain of which is shown in FIG. 7a, is traced in FIG. 11 for baseline clamping and, for clamping with missing A2 screw. Two dominant frequencies of 33 and 50 Hz (and its higher harmonics) are clearly seen. The peek frequency of 244 Hz appears that of the second vibration mode of a cantilever beam clamped to a less than perfectly rigid support (theoretical frequency of the second mode is approximately 310 Hz for a beam in plane stress). The main difference between the two plots of FIG. 11 is higher amplitude of the peak frequency at 67.1 Hz upon removal of screw A2. That can be correlated with the major signal change in time domain shown in FIG. 7a. Marginal shift of the frequency from 244 to 241 Hz can also be noticed in FIG. 11

A similar comparison of FFT plots of the recordings at station 5, for baseline clamping and for two cases of missing screws A1 and A2, shown in FIG. 7b, reveals almost identical curves. The recording at station 5 can be considered as data from a representative location commonly used in vibration-based methods. Only few marginal variations are detectable (and therefore not shown here): shift of the 244 Hz peak frequency to 241 Hz and slightly larger amplitude of a peak at 67 Hz. This agrees with the known observation that the lowest natural vibration frequencies exhibit only low sensitivity to end conditions.

The possibility to identify changes in end data details through measurements of surface strain, in the close vicinity to the joint; has been examined. Strains were measured by standard gauges while the joint condition was controlled by loosening and retightening of screws. It was demonstrated that it is feasible to detect loss of one screw out of six and even to detect intermediate levels of loosening of the screws. Only marginal changes in natural frequencies were observed in far-field, measurements. It appears that it is more effective to establish health monitoring, either in the time or in frequency domains, on measurements taken from, the field near to the joint. Commercially available, simple wave generators are believed to provide similar results, with even better repeatability; and with improved overall sensitivity of the method.

The nature of Lamb waves and of evanescent modes restricts application of the suggested method to joints connecting plate-like (or beam-like), structural members. The end effect sensitivity demonstrated here can be used as a joint signature for identification of incipient damage or deterioration and for a variety of joint types: bolted, welded, bonded, or riveted. Such sensitivity of the evanescent waves can be used for any other damage generating evanescent waves, such as cracks and delaminations. High sensitivity is what makes the suggested method attractive and applicable in detecting early stages of damage.

The health monitoring method suggested here is of local nature, so there is probably a limit on the number of joints that can be monitored. Nevertheless, the sensitivity of end effects, found here in reflecting joint integrity, renders this method a good candidate to be used as a supplementary diagnostic method for critical joints. The procedure can be integrated into a global SHM system envisioned for future structures (e.g., Ref. [18]).

System and Method for Joint Health Monitoring, Verification and Flaw Identification.

Figure 12:
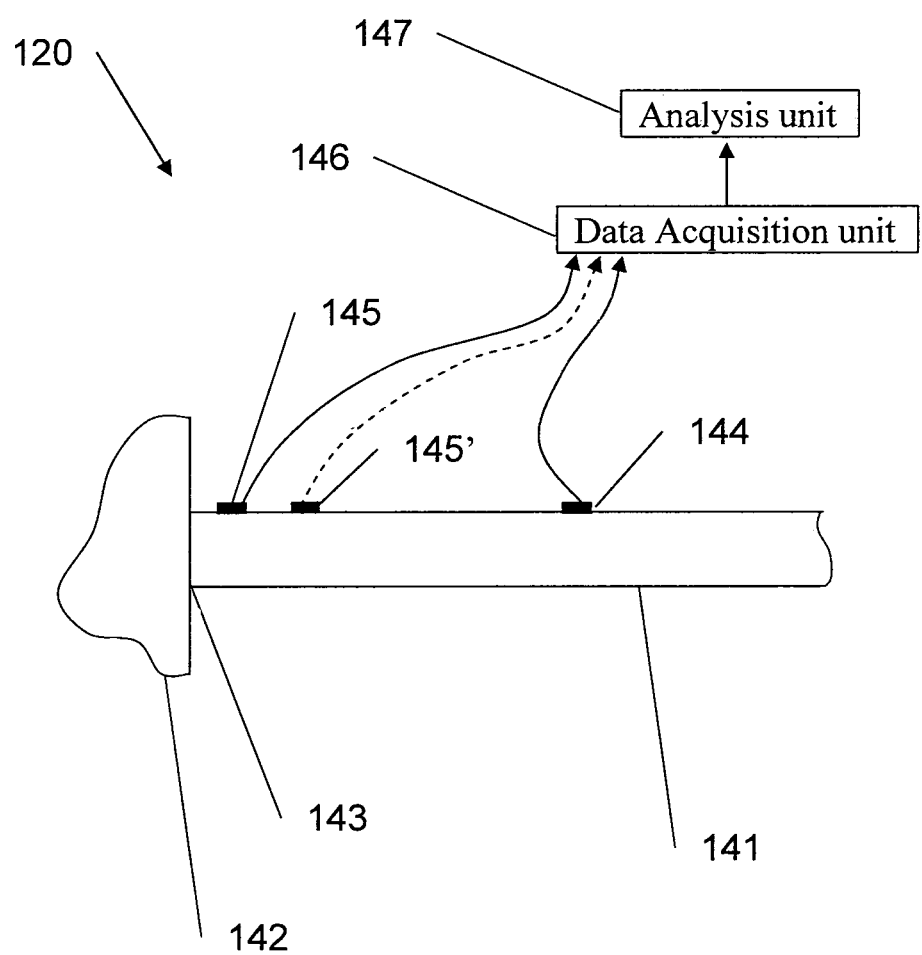
FIG. 12: Schematically depicts a view of the joint area to be monitored and the monitoring system according to an exemplary embodiment of the invention.

FIG. 12 schematically depicts a monitoring system 120 which may be used for monitoring health of a joint, according to an embodiment of the invention.

The joint to be monitored, 143 is schematically depicted as a joint of beam 141 and base structure 142. It should be noted that the terms "beam" is used in the most general way and beam 141 may be a rod, a sheet, or any other structural member having at least one dimension substantially longer than at least one other dimension. It is also be noted that beam141 may be curved or having varying thickness. It can also be made of any material, such as metal, ceramic, and composite. Similarly, the term "base" 142 is used in the most general way and base 142 may be a rod, a sheet, or any other structural member. Similarly, the term "joint" 143 is used in the most general way as already discussed.

In the exemplary embodiment of the invention, at least one near-field strain measuring device 145 is placed in proximity to the monitored joint 143. At least one far-field strain measuring device 144 is placed in location removed from the monitored joint, wherein "near" and "far" were already described as at distance similar or smaller than the narrow dimension of beam 141; and substantially at larger distance than the narrow dimension of beam 141 from joint 143.

Preferably, the near field strain measuring device 145 is placed near enough such that the measured strain is affected by detailed condition of the monitored joint, while far field measuring device is located far enough from the joint so as to be affected by the general perturbation applied to the structure.

Optionally, a plurality of near-field strain measuring devices, is used, for example an optional second near-field strain measuring devices 145'. Similarly, more than one far-field strain measuring devices may be used.

The source of the perturbation is not shown in this figure, but is generally applied at location farther from the joint than the location of the far field strain measuring device. For example, a static load, such as a weight may be attached to the beam 141. In some embodiments, static load is applied. In other embodiments, transient load or cyclic load is applied. The load may be applied due to normal operation of the structure, or intentionally.

Strain measuring devices 145 and 144 are wired, or connected wirelessly to data acquisition unit 146. Preferably, signal conditioning such as noise reduction and digitization is performed by the data acquisition unit and results are transferred to analysis unit 147. Analysis unit 147 may be a dedicated processor or, a general purpose computer such as a PC.

Far field strain measuring device144 gives indication to perturbation applied to the structure and may be used to calibrate the response of the joint, as indicated by signal from the near field strain measurement device, to the perturbation. Analysis unit 147 may be locally positioned. Alternatively, analysis unit 147 is remotely located embodiments, data is stored to be analyzed, in later time.

In some embodiments, strain measuring devices 145 and 144 are attached to beam 142. Alternatively or additionally, strain measuring devices may be attached for the duration of the measurement.

In some embodiments, data acquiring 146 and analysis unit 147 are permanently attached to strain measuring devices 145 and 144. Alternatively, data acquiring 146 and/or analysis unit 147 may be attached for the duration of the measurement.

The monitoring system 120 in FIG. 12 can be used as is to detect edge delaminations within the structural member 141, which can occur due to stress singularities at the joint. This is even if the joint condition itself remained un altered by such delamination. Additionally, same system 120 can be employed to detect end delamination of composites (that might occur due to wave reflections from the end) with only difference from FIG. 12 is the absence of the "base" 142.

Figure 13:
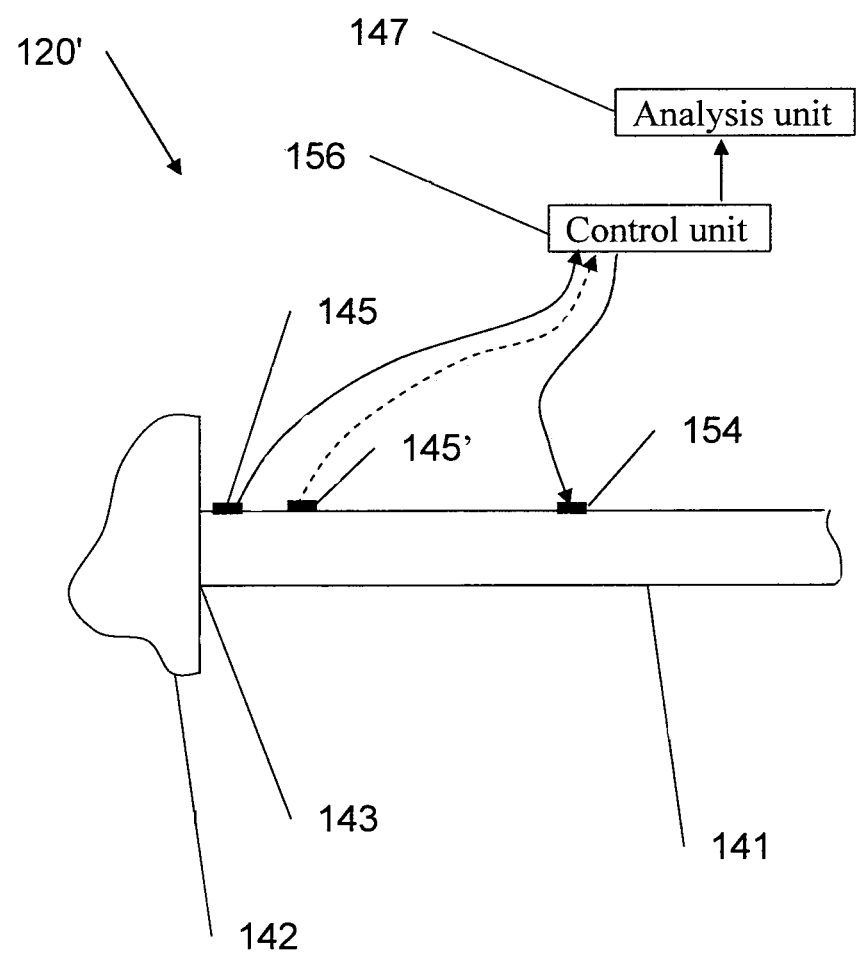
FIG. 13: Schematically depicts a view of the joint area to, be monitored and the monitoring system according to another exemplary embodiment of the invention.

FIG. 13 schematically depicts a monitoring system 120' which may be used for a monitoring health of a joint, according to an embodiment of the invention.

In contrast to the system of FIG. 12, where a perturbation is applied externally, and the ratio of at least two measuring devices is analyzed, in the system of FIG. 13, a known perturbation is applied to the system by an actuator 154 located far from the monitored joint. Preferably, actuator 154 is a PZT actuator, connected to a signal generator within control unit 156. Control unit 156 in this figure is understood to include the functionality of data unit 146; however, separate units may be used. Optionally, sinusoidal signal is used Optionally, plurality of frequencies is used. Alternatively, the signal comprises pulses.

Optionally, system 120' also comprises at least one far-field strain sensor (not shown here). A far field strain sensor may be used for calibration of the stress applied by actuator 154, or for compensation of unintentional stresses caused by the experimental environment.

Figure 14:
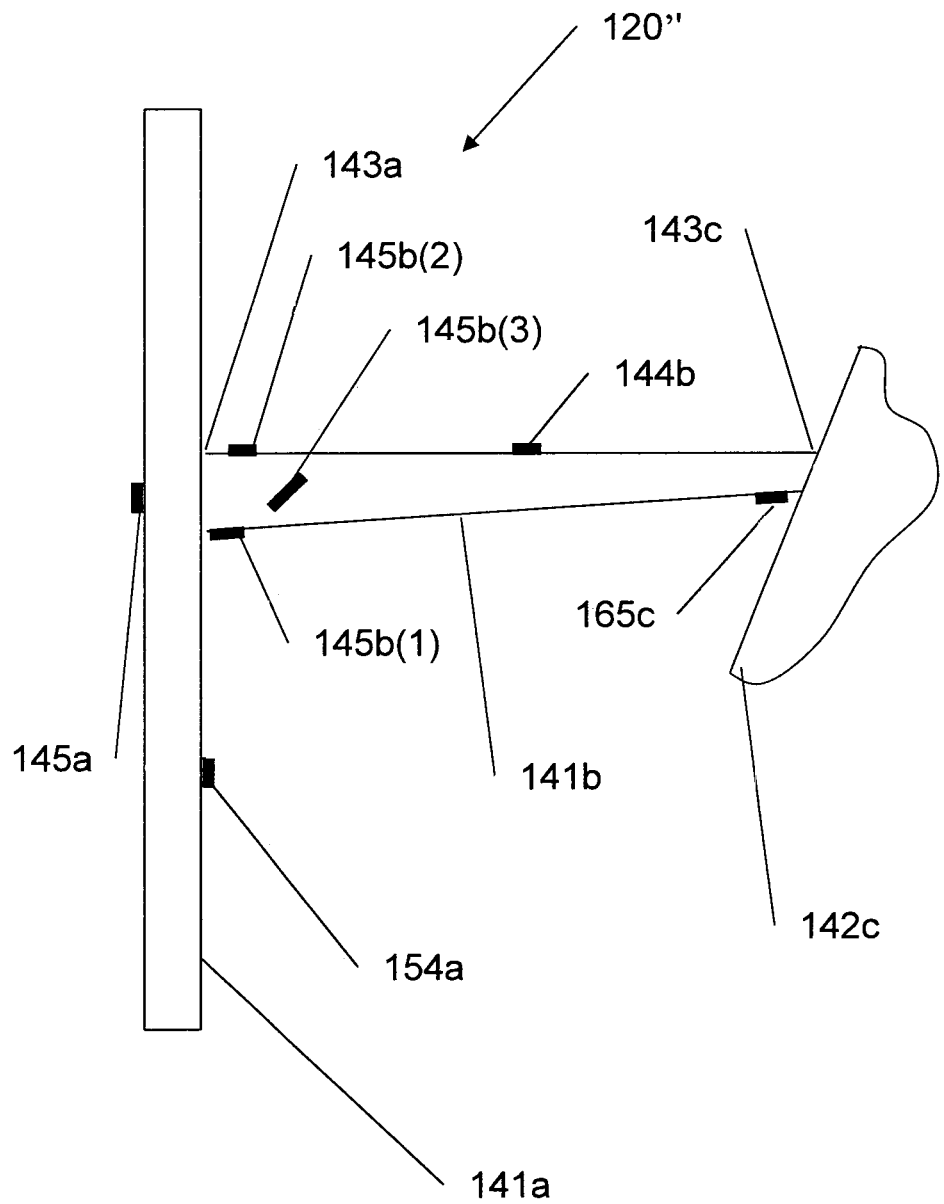
FIG. 14: Schematically depicts a view of the joint area to be monitored and the monitoring system according to yet another embodiment of the invention.

FIG. 14 schematically: depicts a more general schematic view of the joint area to be monitored and the monitoring system 120" according to yet another embodiment of the invention.

According to this embodiment of the invention, a structural member 141b having more than one joint (143a and 143c) may be monitored. In such structure, all, or only one, or few critical joints may be monitored by placing at least one near field strain measuring device near the monitored joint.

Note that FIG. 14 depicts a central beam 141b anchored at both ends for demonstration only. In this figure, central beam 141b is attached to beam 141a by a joint 143a and to base 142c at joint 143c.

Generally, a beam; a rod; a pipe or a plate supported at one end or at more than one end (such as a plate supported at plurality of places) may be monitored. Similarly, a more complex structure having more than two joints or more than three members may be monitored. Not all joints need to be monitored.

Optionally; plurality of near field strain measuring devices (145a, 145b(1-3), 145c, etc) are placed at different distances from the joint. Optionally, said plurality of strain measuring devices 145 are placed at different orientation or at different positions in relation to the joint.

In one specific example of FIG. 14, first [145b(1)] and second [145b(2)] near field strain measurement devices are located at opposite side's of the jointed member 141b, while a third [145b(3)] sensor is oriented at an angle to the beam and positioned on its side face of beam 141b.

Since defects, such as cracks or corrosion damage, are often develop at the surface of the joint, the effect of such defect is different for the opposing measurement devices. Comparing the signals from plurality of such measuring devices may be sensitive to such asymmetric faults. In some embodiments, signals from opposing strain measuring devices may be subtracted at the data processing stage or analog signals may electronically subtracted.

In example of FIG. 14, information about the perturbation is obtained from at least one far field stress indicator device 144b located far the monitored joint. Optionally, signals from same far field stress indicator device 144b are used to monitor health of more than one joint, for example joints 143a and 143b. Alternatively, more than one far field stress indicator devices 144 are used. Optionally, signals from plurality of far, field stress indicator devices 144 are combined, for example for noise reduction purposes.

In the example of FIG. 14, a side beam 141a is joined to central beam 141b in joint 143a. In this embodiment, health of, joint 143a is also monitored by near-field strain sensor 145a while excitation is. Provided by actuator 154a.

The stress indicator may be a strain measuring device such as in FIG. 12. Alternatively, a strain measuring device measuring the motion of the member due to applied stress may be used. Alternatively, an accelerometer may be used. Optionally, first or second integration of the acceleration may be used as indication of evanescent waves. Alternatively, an actuator may be used as strain indicator as in FIG. 13. It should be noted that combination of such alternatives may be used.

It should be noted, that loads that applied to the structure during normal use may be used. For example, changes in stress due to car passing on a bridge may be assessed by a far field indicator attached to the bridge span, and their reading compared to signals from near field strain measuring devices located near the bridge's joints in order to monitor the integrity of the joints without having to apply external perturbation. Similarly, vibration naturally occurring in a working machine such as an airplane may be used as perturbation. For example, a test may be performed while an airplane is the ground with engines working or while in the air.

For example, temperature changes may change the quasistatic load on a structure. That temperature effect is eliminated by the use of the far field calibrating measurement.

Transient loads may be applied by striking the structure. Cyclic loads may be applied to induce vibration of the structure.

Monitoring system may be installed for the test duration and removed after the test. Alternatively, at least part of the monitoring equipment may stay on the system. Alternatively, at least parts of the monitoring equipment may be built into the system or permanently installed.

Few exemplary monitoring procedures according to exemplary embodiment of the invention are presented:

1. A method for monitoring health of a joint using static load.

According to an exemplary embodiment of the invention, a method for monitoring health of a joint using static load comprises the steps of:

At virgin state of the system, create reference plots of the near and far field gauges recordings for several (at least two) levels of static loading. The plot preferably correlates the far field as the abscissa with the near field response as ordinate. The static loading preferably imitates the static loading that will be used subsequently for inspection.

For inspection, load the structure and record the strains in the near and the far fields.

Find from the reference plot the near field reading appropriate to the far field recorded in the inspection test.

Compare that value from the reference plot with the near field recording obtained in the inspection test.

If the difference is larger than some predetermined value-infer that damage to the joint has occurred.

2. A method for monitoring health of a joint using dynamic load.

According to an exemplary embodiment of the invention, a method for monitoring health of a joint using dynamic load comprises the steps of:

At virgin state of the system, create a plurality of reference plots, of the near field gauges time-dependent recording for several levels of excitation of the excitation device. The excitation preferably covers the excitation intensity subsequently to be used for test.

For inspection, induce excitation in the load excitation device and record the strain response in the near field gauge.

Find from the reference plot the near field reading appropriate to the excitation applied in the inspection test.

Compare that strain history recording from the reference plots with the near field recording obtained in the test for the same excitation level.

If the difference is larger than some predetermined value-infer that damage to the joint has occurred.

3. A method for monitoring health of a joint using vibration.

According to an exemplary embodiment of the invention, a method for monitoring health of a joint using vibration comprises the steps of:

At virgin state of the system, create reference plots of the near and far field gauges recordings, for a plurality of levels of vibration of the structure. The plot preferably correlates the far field amplitude as the abscissa with the near field amplitude as ordinate. The vibration conditions preferably cover the conditions that will be used subsequently for inspection. Optionally, plurality of frequencies are used. Optionally, frequency range includes natural resonance frequency(s) of the structure.

For inspection, while the structure vibrates record the amplitude of the strains in the near and the far fields. Excitation of the vibration may be an actuator or normally occurring vibration.

Find from the reference plot the near field amplitude appropriate to the far field amplitude obtained in the inspection test.

Compare that value from the reference plot with the near field recording obtained in the inspection test. Comparing values may comprise comparing ratio of amplitudes of reading from at least two sensors. Comparing values may comprise comparing phase between cyclic excitation and sensor reading or between readings of plurality of sensor. Comparing values may comprise comparing reading at several frequencies.

If the difference is larger than some predetermined value-infer that damage to the joint has occurred.

A "virgin state" of a system can refer also to an existing working structure. Then, the first step of generation of reference plots marks the baseline for future measurements and should be evaluated and confirmed as a preferred condition of the system. Optionally, "virgin state" of a system can refer also to the state of a separate calibration structure known to be in nominal condition. Optionally, recording of "virgin state" of a system can refer to an average of several recordings from plurality of calibration structures known to be in nominal condition.

Another aspect of the invention of the invention, the system may be used to identify flaws in the monitored joint.

For example; some types of joins are susceptible to weakness in specific locations such as welds, gluing, bolts, or locations were stress is concentrated. In another example, riveted, fastened or screwed joint may be missing one or few of the rivets, screws, bolts or fastener, or one or few of the rivets, screws or fastener may be loose. In these joints, there are a finite number of flaws which are likely to occur.

In this case, the signature of a weak joint may be studied as well as the signature of a nominal joint. Studying the signature of a weak and/or nominal joint may be done by experimentation by intentionally weakening the joint, or by computation, for example finite element analysis. For example in a joint having N bolts, the signal signatures of a joint having only N−1 bolt may be calculated or measured. Additionally, the N*(N−1) cases of two missing bolts may also be studied.

By comparing the measured signal from a monitored joint to the library of signals comprising signals representing nominal ad plurality of weak joints, the type of weakness may be ascertained.

A practical use of such embodiment may be the testing a joint after production, or after reassembly as routine or scheduled test. For example, joints connecting airplane's engine may be tested anytime the engine is replaced or removed for maintenance to verify the integrity the joint, and the correct assembly of the joint.

It should be noted that some type of excitation and specific location or orientation of near field strain sensor may yield larger differences among signature signals. In some embodiments of the invention, prior analysis of nominal and flawed structure is used to optimize at least one of location of at least one near field strain sensor, orientation of at least one near field strain sensor; number of near field strain sensors and at least one parameter of the perturbation such as location of at least one far field stress indicator; orientation of least one far field stress indicator; frequency of excitation; etc.

In another, embodiment symmetry of the joint is likely to be altered by, weakening. For example, a joint having even number of bolts becomes non-symmetric if one bolt is missing or loose. This symmetry breaking may be exploited when designing the joint or placing sensors and/or indicators.

In another example depicted in FIG. 3, a third strain sensor is optionally installed near the first monitored joint. As can clearly be seen, said strain sensor is oriented non-collinearly with the stress indicator. It should be noted that naming the strain sensors as "first", "second" and "third" is done for convenience only, and their order is arbitrary.

It should be noted that while each monitored joint is associated with at least one near field strain measuring device, the number of stress indicators (actuators or far field strain sensors) may be smaller than the number of monitored joints.

In some embodiments, data processing comprises of frequency domain analysis of the signal. For example signal analyzer may be used. In one embodiment, Fourier analysis of the ratio of the hear field strain to the applied perturbation is performed. Optionally; phase as well as amplitude response are analyzed.

In some embodiments of the invention, harmonics analysis is performed. For example, asymmetric response of a joint, due for example to a fault at one side of the joint may cause a strong second harmonics in the resulted measured strain, thus creating vibration at high harmonic frequencies, for example at twice the excitation frequency or higher harmonics. Additionally, such a fault may cause the second harmonics to largely be out of phase with the perturbation.

It should be noted, that strain measuring devices and/or stress indicators may be connected to data acquisition systems using electrical wires. Alternatively, wireless or fiber-optics systems may be used.

Optionally, data may be digitized, transferred to a remote location, or stored for off-line analysis.

In any of the embodiments, near field strain measuring device and/or far field strain measuring device may be chosen from a group comprising: strain gauge; PZT transducer; ultrasonic sensor; non-contact speckle interferometry; holography; etc. Different type of devices may be used in the same system.

In any of the embodiments, excitation of perturbation may be done using: ultrasonic contact PZT; electromechanical device such as solenoid or a speaker; un-balanced rotating rotor; non-contact laser pulses causing thermal expansion; non-contact electro magnetic forces induced on conductive or magnetic structural parts. It should be noted that stress produced in vicinity of a joint may be used as far field stress for another joint.

In any of the embodiments, a; joint is a location connecting at least one part of following: Beam-like part; Plate-like part; Rod like part or a Pipe-like part. Alternatively, free end, is considered as "joint" for the purpose of present invention.

In any of the embodiments, any damage to the joint may be one of the following: missing or damage to the connecting media such as rivets, bolts; bonding material such as glue, or weakening of the joint due to de-bonding, cracks in the weld; corrosion; loose bolt/nuts; cracks in the vicinity of the joint; material fatigue; plastic yield caused for example by overloading; delaminting of composite material or structure; etc.

It should be noted the disclosed method and system may be used in operational conditions of the structure such as: stationary loaded structure; unloaded structure; vibrating structure or in zero gravity such as spacecrafts.

It is appreciated that certain features of the invention, which are, for clarity, described in the context of separate embodiments, may also be provided in combination in a single embodiment. Conversely, various, features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification incorporated in their entirety by reference into the specification, to the same extent as if each individual publication, patent or patent application was specifically and individually indicated to be incorporated herein by reference. In addition citation or identification of any reference in this application shall not be construed as an admission that such reference is available as prior art to the present invention.

The invention claimed is:

1. A system for monitoring joints comprising:
at least one joined member, having a width, wherein said joined member is joined to a structure by a monitored joint;
at least one near field strain measuring device located on said joined member, within a distance of less than the width of said joined member from said monitored joint;
at least one far field strain measuring device located on said joined member, at a distance of more than twice the width of said joined member away form said monitored joint; and
a computerized processor configured to;
receive data indicative of strain at said near field strain measuring device and said far field strain measuring device;
compute monitored signal signature based on the ratio of the data received from said near field strain measuring device and data received from said far field strain measuring device;
compare the monitored signal signature to a stored signal signature of a healthy joint; and
determine the integrity of said monitored joint based on the comparison of the monitored signal signature to the signal signature of a healthy joint.

2. The system of claim 1, wherein said near field, strain measuring device is a strain gage.

3. The system of claim 1, wherein said far field strain measuring device is a strain gage.

4. The system of claim 1, wherein at least one of said far field strain measuring device and said near field measuring device is a position sensor.

5. The system of claim 1, wherein at least one of said far field strain device and said near field measuring device is an accelerometer.

6. The system of claim 1, wherein said far field strain measuring device is an actuator.

7. The system of claim 6, wherein the actuator is a PZT actuator.

8. The system of claim 1 further comprising a second near field strain measuring device installed on said joined member, within a distance of less than width of said joined member from said monitored joint.

9. The system of claim 1 further comprising a second near field strain measuring device,
wherein said joined member is jointed to a second structure by a second monitored joint, and
wherein said second near field strain device is installed on said joined member, within a distance of less than the width of said joined member from said second monitored joint.

10. The system of claim 1, wherein monitoring joints comprises comparing readings of a near field strain measuring device and a far field strain measuring device to readings from an undamaged joint similar to the monitored joint.

11. The system of claim 1, wherein monitoring joints comprises comparing readings of a near field strain measuring device and a far field strain measuring device to stored readings from said monitored joint.

12. The system of claim 1, wherein monitoring joints comprises comparing readings of a near field strain measuring device and a far field strain measuring device to computed readings from mathematical model of the monitored joint.

13. A method for monitoring joints comprising:
receiving by a computerized processor data from at least one near field strain measuring device and at least one far field strain measuring device, positioned on a joined member, wherein:
said at least one joined member is joined to a structure by a monitored joint,
said at least one near field strain measuring device is located on said joined member, within a distance of less than the width of said joined member from a monitored joint, and
said at least one far field strain measuring device is located on said joined member, at distance of more than twice the width of said joined member from said monitored joint,
computing a monitored signal signature based on the ratio of the data received from said near field strain measuring device and the data received from said far field strain measuring device;
comparing the monitored signal signature to a stored signal signature of a healthy joint; and
determining an integrity of said monitored joint based on the comparison of the monitored signal signature to the signal signature of a healthy joint.

14. The method of claim 13, wherein said applied stress is static.

15. The method of claim 13, wherein said applied stress is dynamic.

16. The method of claim 13, wherein said applied stress is repetitive.

17. The method of claim 16, wherein said applied stress is harmonic.

18. The method of claim 13, wherein said applied stress is externally applied.

19. The method of claim 13, wherein said applied stress is caused by routine operation of said joint.

20. A method for identifying flaws in joint comprising:
   receiving by a computerized processor data from at least one near field strain measuring device and at least one far field strain measuring device positioned on a joined member, wherein:
      said at least one joined member is jointed to a structure by a monitored joint,
      said at least one near field strain measuring device is located on said joined member, within a distance of less than the width of said joined member from a monitored joint, and
   said at least one far field strain measuring device is located on said joined member, at distance of more than twice the width of said joined member from said monitored joint;
   providing a signal signature of a healthy joint, substantially the type of said monitored joint, wherein said signal signature of a healthy joint is computed from the ratio of the data received from a near field strain measuring device and data received from a far field strain measuring device when stress is applied on a healthy joint substantially the type of said monitored joint;
   providing a plurality of flawed signal signatures indicative of a differently flawed joint, wherein each of said flawed signal signatures is computed from the ratio of the data received from a near field strain measuring device and data received from a far field strain measuring device when stress is applied on a flawed joint substantially the type of said monitored joint;
   acquiring signals from said at least one near field strain measuring device and said at least one far field strain measuring device, while said monitored joint is under stress;
   computing monitored signal signature based on the ratio of the data received from said near field strain measuring device data received from said far field strain measuring device;
   comparing said monitored signal signature with said signal signature of a healthy joint and said plurality of said signal signatures of a differently flawed joint; and
   determining if said joint is healthy or flawed, and if flawed, which is the likely flaw.

21. The method of claim 20, wherein said applied stress is caused by routine operation of said joint.

22. The system of claim 1, wherein said joined member is a beam.

23. The system of claim 1, wherein said joined member is a plate.

24. The method of claim 13, wherein said joined member is a beam.

25. The method of claim 13, wherein said joined member is a plate.

* * * * *